US011629337B2

(12) United States Patent
Czernichow

(10) Patent No.: US 11,629,337 B2
(45) Date of Patent: Apr. 18, 2023

(54) PRODUCTION OF A CANINE BETA CELL LINE FROM AN IMMATURE PANCREAS

(71) Applicant: ANIMAL CELL THERAPY—ACT, Paris (FR)

(72) Inventor: Paul Czernichow, Paris (FR)

(73) Assignee: ANIMAL CELL THERAPY—ACT, Paris (FR)

( * ) Notice: Subject to any disclaimer, the term of this patent is extended or adjusted under 35 U.S.C. 154(b) by 1078 days.

(21) Appl. No.: 16/300,310

(22) PCT Filed: May 11, 2017

(86) PCT No.: PCT/EP2017/061401
§ 371 (c)(1),
(2) Date: Nov. 9, 2018

(87) PCT Pub. No.: WO2017/194711
PCT Pub. Date: Nov. 16, 2017

(65) Prior Publication Data
US 2019/0367881 A1 Dec. 5, 2019

Related U.S. Application Data

(60) Provisional application No. 62/334,738, filed on May 11, 2016.

(51) Int. Cl.
*C12N 5/071* (2010.01)
*C12N 5/09* (2010.01)
*G01N 33/569* (2006.01)

(52) U.S. Cl.
CPC ......... *C12N 5/0676* (2013.01); *C12N 5/0693* (2013.01); *G01N 33/56966* (2013.01); *C12N 2503/02* (2013.01); *C12N 2503/04* (2013.01)

(58) Field of Classification Search
CPC .............. C12N 5/0676; C12N 2510/04; G01N 33/56966
USPC ....................................................... 435/350
See application file for complete search history.

(56) References Cited

U.S. PATENT DOCUMENTS 6,429,013 B1  8/2002  Halvorsen et al.
6,777,231 B1  8/2004  Katz et al.
8,735,154 B2  5/2014  Berkland et al.

FOREIGN PATENT DOCUMENTS

| EP | 1947193 A1 | 7/2008 |
|---|---|---|
| WO | WO 01/38548 A2 | 5/2001 |
| WO | WO 01/88102 A1 | 11/2001 |
| WO | WO 02/092756 A2 | 11/2002 |
| WO | WO 2008/102000 A1 | 8/2008 |
| WO | WO 2009/132173 A2 | 10/2009 |
| WO | WO 2013/057164 A1 | 4/2013 |

OTHER PUBLICATIONS

Vrabelova (2014, Veterinary Surgery, 43:631-641).*
Pretzer, 2014, Veterinary Surgery, 43:631-641.*
Ahlgren et al., "Lack of Evidence for a Role of Islet Autoimmunity in the Aetiology of Canine Diabetes Mellitus", PLOS One, vol. 9, No. 8, Aug. 2014, pp. 1-7.
Aspinwall et al., "Insulin-stimulated Insulin Secretion in Single Pancreatic Beta Cells", The Journal of Biological Chemistry, vol. 274, No. 10, Mar. 5, 1999, pp. 6360-6365 (6 pages).
Bonnett et al., "Age Patterns of Disease and Death in Insured Swedish Dogs, Cats and Horses", J.Comp. Path, vol. 142, 2010, pp. S33-S38 (6 pages).
Bricout-Neveu et al., "Development of the Endocrine Pancreas in the Beagle Dog: From Fetal to Adult Life", The Anatomical Record, vol. 300, 2017 (published online Mar. 14, 2017), pp. 1429-1438 (10 pages).
Castaing et al., "Ex Vivo Analysis of Acinar and Endocrine Cell Development in the Human Embryonic Pancreas", Developmental Dynamics, vol. 234, 2005pp. 339-345 (7 pages).
Catchpole et al., "Canine diabetes mellitus: can old dogs teach us new tricks?", Diabetologia, vol. 48, 2005 (published online Sep. 8, 2005), pp. 1948-1956 (9 pages).
Davison et al., "Autoantibodies to GAD65 and IA-2 in canine diabetes mellitus", Veterinary Immunology and Immunopathology, vol. 126, 2008, pp. 83-90 (8 pages).
Davison et al., "Study of 253 dogs in the United Kingdom with diabetes mellitus", The Veterinary Record, vol. 156, 2005, pp. 467-471 (7 pages).
Džaja et al., "Insulinoma in a dog: case report", Veterinarski Arhiv, vol. 70, No. 1, 2000, pp. 13-20 (8 pages).
Gale, "Do dogs develop autoimmune diabetes?", Diabetologia, vol. 48, 2005 (published online Aug. 19, 2005), pp. 1945-1947(3 pages).
Hawkins et al., "Immunocytochemistry of Normal Pancreatic Islets and Spontaneous Islet Cell Tumors in Dogs", Vet. Pathol., vol. 24, 1987, pp. 170-179 (10 pages).

(Continued)

*Primary Examiner* — Valarie E Bertoglio
(74) *Attorney, Agent, or Firm* — Birch, Stewart, Kolasch & Birch, LLP

(57) ABSTRACT

The present invention relates to a method for preparing commercial scale quantities of canine functional beta cells and to the establishment of cell lines from immature canine pancreatic tissues. It also relates to a method of diagnosis using canine beta cell tumours or cells derived thereof. The method comprises sub-transplantation procedure to enrich the graft in proliferating beta cells, allowing generating canine Beta cell lines. Such lines express, produce and secrete insulin upon glucose stimulation.

12 Claims, 8 Drawing Sheets

(56) References Cited

OTHER PUBLICATIONS

Figure 1:
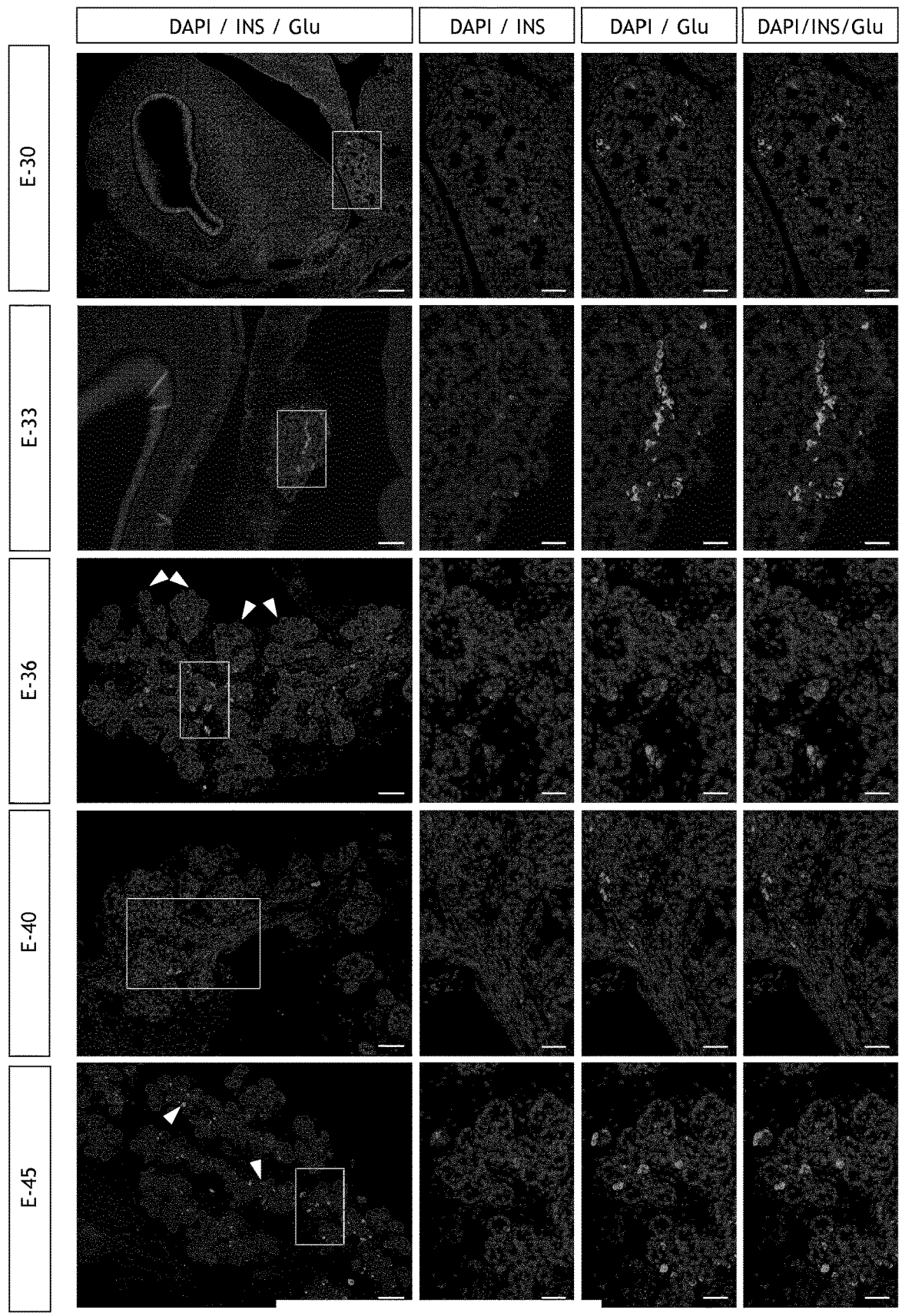

International Search Report and Written Opinion of the International Searching Authority, for Application No. PCT/EP2017/061401, dated Jul. 28, 2017.

Justice et al., "Etude Morphometrique Des Ilots De Langerhans Du Pancreas De Chien Beagle", Rev. Fr. Histotechnol., vol. 10, No. 1, 1997, pp. 45-49 (5 pages).

Kennedy et al., "Identification of susceptibility and protective major histocompatibility complex haplotypes in canine diabetes mellitus," Tissue Antigens, vol. 68, No. 6, 2006, pp. 467-476 (11 pages).

Khalfallah et al., "Zinc Finger Protein 191 (ZNF191/Zfp191) is Necessary to Maintain Neural Cells as Cycling Progenitors", Stem Cells, vol. 27, 2009, pp. 1643-1653 (12 pages).

Kim et al., "Islet architecture: a comparative study", Islets, vol. 1, No. 2, Sep. 2009, pp. 129-136 (12 pages).

Nelson et al., "Animal models of disease: classification and etiology of diabetes in dogs and cats", Journal of Endocrinology, vol. 222, No. 3, 2014, pp. T1-T9 (10 pages).

Niessen et al., "Evaluation of a Quality-of-Life Tool for Dogs with Diabetes Mellitus", J. Vet. Intern. Med, vol. 26, 2012, pp. 953-961 (10 pages).

Pictet et al., "An Ultrastructural Analysis of the Developing Embryonic Pancreas", Developmental Biology, vol. 29, 1972, pp. 436-467 (32 pages).

Rand et al., "Canine and Feline Diabetes Mellitus: Nature of Nurture?", The Journal of Nutrition, vol. 134, No. 8, 2004, pp. 2072S-2080S (9 pages).

Ravassard et al., "A genetically engineered human pancreatic β cell line exhibiting glucose-inducible insulin secretion", The Journal of Clinical Investigation, vol. 121, No. 9, Sep. 2011, pp. 3589-3597 (9 pages).

Ravassard et al., "A New Strategy to Generate Functional Insulin-Producing Cell Lines by Somatic Gene Transfer into Pancreatic Progenitors", PLOS One, vol. 4, No. 3, Mar. 2009, pp. 1-9 (9 pages).

Russ et al., "In Vitro Proliferation of Cells Derived From Adult Human βCells Revealed By Cell-Lineage Tracing", Diabetes, vol. 57, Jun. 2008, pp. 1575-1583 (9 pages).

Scharfmann et al., "β-cell development: the role of intercellular signals", Diabetes, Obesity and Metabolism, vol. 10, Supplemental 4, 2008, pp. 195-200 (6 pages).

Shields et al., "Extreme Beta-Cell Deficiency in Pancreata of Dogs with Canine Diabetes", PLOS One, vol. 10, No. 6, Jun. 9, 2015, pp. 1-19 (19 pages).

Steiner et al., "Pancreatic islet plasticity: Interspecies comparison of islet architecture and composition", Islets, vol. 2, No. 3, May 2010, pp. 135-145 (20 pages).

Zufferey et al., "Multiply attenuated lentiviral vector achieves efficient gene delivery in vivo", Nature Biotechnology, vol. 15, Sep. 1997, pp. 871-875 (5 pages).

\* cited by examiner

PRODUCTION OF A CANINE BETA CELL LINE FROM AN IMMATURE PANCREAS

The present invention relates to a method for preparing canine beta cells in vitro from pancreatic tissue. It particularly concerns obtaining insulin secreting cells from pancreas obtained during the pre-natal period. It also relates to methods of diagnosis of canine diabetes using beta cell tumours or cells derived thereof.

BACKGROUND OF THE INVENTION

Canine Diabetes, a Common Condition without an Ideal Treatment

The prevalence of canine diabetes, and diabetes in pet animals in general, has only been studied in recent years, especially at the epidemiological level. Nonetheless, the prevalence of animal diabetes increases, as in humans. Veterinarians estimate that the frequency of canine diabetes has tripled in 30 years in Europe and the USA. The causes of dog diabetes, however, have not been further characterized. As a consequence, canine diabetes is often diagnosed late in the disease course.

The most common form of diabetes in dogs resembles type 1 diabetes in humans, although other types of diabetes have also been described in dogs (Nelson and Reusch, 2014; Rand et al., 2004; Bonnet et al., 2010; Catchpole et al., 2005; Shield et al, 2015; Ahlgren et al., 2014; Davison et al., 2008; Kennedy et al., 2006; Gale, 2005).

Only one effective treatment, consisting in daily insulin injections, is available for all types of diabetes in dogs. Typically, a dog will receive a dose of about 1 Insulin Units (IU)/kg once per day (Davison et al., 2005). Such a treatment represents a significant financial burden and results in a significant deterioration in the quality of life (Niessen et al., 2012).

In this context, there is a need for new, more effective and less heavy treatment. In this respect, cell therapy is clearly advantageous, as it may offer nearly unlimited source of either pluripotent or adult cells, that have the potential to be highly compatible with the animal to be treated.

Cell Therapy and Veterinary Medicine

The treatment of chronic diseases or of injuries of domestic animals by cell therapy is already implemented in the veterinary field.

For example, treatments using stem cells isolated from fat tissue (adipose), collected on the domestic animal to be treated, have been recently developed (U.S. Pat. No. 6,777,231 B1, U.S. Pat. No. 6,429,013 B1). These adipose-derived stem cells are administered to diseased or damaged cartilages, tendons and joints of the domestic animal to be treated, and are intended to regenerate the damaged tissue (for example VetStem Regenerative Cells: VSRC™, developed by the company "Vet-Stem Biopharma").

However, these stem cell-based therapies are not applied to diabetes and other endocrine disorders.

In the field of diabetes, advances in cell therapy remain modest despite a developing interest in therapy "replacement" for the pet animals, mainly dogs and cats. In particular, pet animal organ harvesting networks have been developed, leading to the creation of organ libraries. Islets of Langerhans can be collected from donated animal pancreases and stored by cryopreservation before being transplanted to compatible acceptor diabetic animal (U.S. Pat. No. 8,735,154 B2). The transplant of such cryopreserved Islets of Langerhans is intended to replace insulin injections in grafted compatible diabetic animals (for example Kanslet™ developed for cats and dogs by LIKARDA LLC).

This important progress in animal diabetes therapy is however limited by several outstanding issues. In particular, collected and frozen Islets of Langerhans cannot be expanded, so the amount of islets available is strictly dependent on the amount collected on each organ.

In a first step towards developing a cellular therapy of canine diabetes, it would be extremely useful to have canine beta cell lines which can be maintained and expanded in vitro.

Pancreas Physiology and Pancreatic Beta Cells

The mammal mature pancreas contains two types of tissue: exocrine tissue composed of acinar cells that produce enzymes (e.g., carboxypeptidase-A) secreted via the pancreatic ducts into the intestine and endocrine tissue, also known as endocrine islets, including islets of Langerhans, composed of cells that produce hormones such as insulin (beta cells), glucagon (alpha cells) somatostatin (delta cells) and pancreatic polypeptide (PP cells).

The ontogeny of the endocrine pancreas during foetal life and the structure of the islets of Langerhans in the adult have been quite extensively studied in mice, rats and humans (Steiner et al., 2010; Kim A et al., 2009; Pictet et al., 1972). By comparison the development of the canine pancreas has been largely ignored. As of today, the development of the canine pancreas at the foetal or the post-natal stages has not been described. In particular, the maturation of the hormone-secreting pancreatic tissues (or endocrine tissue) has not been described, thus preventing the development of successful methods of establishing and maintaining beta cell lines Yet, generation of canine pancreatic beta cells in large amount represents an important objective, because such beta cells could be used for cell therapy of canine diabetes, as explained above. In addition, such pancreatic beta cells would also be useful for screening new drugs that can modulate canine beta cell function and that are adapted for canine diabetes treatment.

Thus, there is still a need for a reliable and reproducible method for developing a functional canine beta cell line.

DESCRIPTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well-known and commonly used in the art. The practice of the present invention employs, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook et al, 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et ah, eds., 1987, and periodic updates); PCR: The Polymerase Chain Reaction, (Mullis et al, ed., 1994); A Practical Guide to Molecular Cloning (Perbal Bernard V., 1988); Phage Display: A Laboratory Manual (Barbas et al., 2001). Enzymatic reactions and purification techniques are performed according to manufacturer's specifications, as commonly accomplished in the art or as described herein.

The present inventors have developed an innovative approach to the generation of canine beta cells which is based on cell therapy.

In a first aspect, the invention provides a method for producing canine pancreatic beta cell lines or canine beta cell tumours. In particular, the invention is directed to a method for producing dog beta cell lines.

As used herein, a "beta cell" is a cell of the islets of Langerhans of the pancreas which secretes the hormone insulin in response to glucose and other secretagogues.

A "canine pancreatic beta cell" or "canine pancreas beta cell" or "canine beta cell" (these terms are synonymous in the context of the present application and should thus be construed to convey the same meaning) is a beta cell of canine origin. Similarly, as used herein, "dog pancreatic beta cell" or "dog pancreas beta cell" or "dog beta cell" is a beta cell of dog origin.

The present inventors have devised a new and innovative strategy for generating canine beta cell lines from immature canine pancreatic tissue materials. They have surprisingly discovered that grafting immature canine pancreatic tissue at a specific developmental stage in a scid mouse results in the development in a fully mature pancreas organ containing both endocrine and exocrine tissue. They have also surprisingly discovered that, by using a sub-grafting method with canine immature pancreatic tissues, the pancreatic cells were capable of forming insulinoma-structures, under specific conditions. These insulinoma-structures contain canine functional beta cells, whose sub-grafting results in a specific enrichment in beta cells, ultimately leading to the production of homogenous, stable and functional canine beta cell lines which can be further amplified to clinical and commercial scale. By repeating the enrichment and amplification steps, the inventors were capable of obtaining repeatedly functional canine beta cell lines which are capable of stably producing canine insulin and can be amplified for testing, diagnosis or therapeutic use.

Accordingly, the present invention relates to a method for specifically establishing and amplifying canine beta cells from canine pancreatic tissues.

Several independent canine beta cell lines have been thus generated. All of them express insulin and are capable of producing canine insulin. Then, canine beta cell lines are capable of responding to glucose stimulation and are therefore fully functional.

This opens perspective towards veterinary use of beta cells in the treatment of canine diabetes. The new process for obtaining insulin-secreting cells by the method of the invention provides an abundant source of canine beta cells. Advantageously, the canine beta cells obtained by said new process are stable and functional canine beta cells.

The canine beta cell lines obtained with the method of the invention can be efficiently used to detect the presence of auto-antibodies found in sera of diabetic canines and thereby have a great potential for diagnosis of canine diabetes. These beta cells are also being used to generate and amplify ad infinitum canine beta cell lines which form master cell batches for canine cellular therapy.

In a first embodiment, the invention is directed to a method for preparing canine pancreatic beta cells or canine beta cell tumours, said method comprising the steps of:

a) transducing and co-transducing immature canine pancreas cells with i) a lentiviral vector expressing SV40 LargeT antigen under the control of the insulin promoter, or ii) with a lentiviral vector expressing SV40 LargeT antigen under the control of the insulin promoter and a lentiviral vector expressing hTert under the control of the insulin promoter, or iii) a lentiviral vector expressing both SV40 LargeT antigen and hTert under the control of the insulin promoter;

b) introducing the transduced immature pancreas cells obtained in a) into the kidney capsule of a first severe combined immunodeficiency (scid) non-human animal;

c) allowing the transduced immature pancreas cells to develop insulinoma-like structures, wherein the immature canine pancreases cells in insulinoma-like structures have differentiated to insulin-producing pancreatic beta cells;

d) micro-dissecting the insulinoma-like structures obtained in step c), and dissociating the cells thereof;

e) sub-transplanting the cells obtained in step d) into the kidney capsule of a second scid non-human animal;

f) allowing the sub-transplanted cells in step e) to develop and regenerate newly developed insulinoma-like structures, wherein said newly developed insulinoma-like structures are enriched in insulin-producing pancreatic beta cells;

g) micro-dissecting the insulinoma-like structures obtained in step f), and dissociating and collecting the cells thereof;

h) optionally, sub-transplanting the cells obtained in step g) into the kidney capsule of a third non-human scid animal, hence allowing further enrichment and amplification of insulin-producing pancreatic beta cells; and i) optionally repeating step e), f) and g) until the appropriate amount of insulin-producing pancreatic beta cells is obtained.

The term "pancreatic tissue" as used herein refers to a tissue obtained or derived from the pancreas; likewise, the term "pancreatic cells" refers herein to cells obtained or derived from pancreas. As used herein, the term "immature pancreatic cells" refers to cells which may be obtained from foetal pancreas or stem cells that have gone through a first differentiation in endodermic cells.

The term "canine" or "canine animal" as used herein refers to any animal member of the Canidae family. The Canidae family includes, but is not restricted to, any race of wolves (*Canis lupus*), dogs (species: *Canis lupus familiaris*), dingos (*Canis lupus*), coyotes (genus *Canis*), lycaons (genus Lycaon), foxes (genus *Canis*, Cerdocyon, Dusycyon, Lycalopex, Otocyon, Drocyon, *Vulpes*) and jackals (genus *Canis*).

Preferably, the canine animal is a dog (species: *Canis lupus familiaris*).

The term "canine pancreatic tissue" as used herein refers to a tissue obtained or derived from the pancreas of any member of the Canidae family; likewise, the term "canine pancreatic cells" or "canine pancreas cells" refers herein to cells obtained or derived from pancreas of any member of the Canidae family. The term "immature canine pancreatic cells" or "immature canine pancreas cells" as used herein refers to cells which may be obtained or derived from foetal pancreas of any member of the Canidae family or stem cells of any member of the Canidae family that have gone through a first differentiation in endodermic cells.

Preferably, the immature canine pancreas cells are immature dog pancreas cells.

As of today, the development of the canine pancreas has never been described, preventing the successful generation of canine pancreatic cell lines. The present inventors were the first one to study the early morphological development of the canine endocrine pancreas (Bricout-Neveu et al., 2017).

Notably, the present inventors were the first to show that the fully mature and insulin-producing structures of the pancreas are observed only in the early post-natal life in the dog. Indeed, the inventors have shown that canine insulin positive cells begin to emerge at mid gestation around 30 days of the foetal life (Bricout-Neveu et al., 2017).

Thus, in one embodiment of the method of the invention, the pancreas cells according to the invention are recovered from at least one a foetal canine pancreas which is in the last third of gestation. Preferably, the pancreas cells according to the invention are recovered from a foetal canine pancreas removed at days 40 to 60 post conception. Yet preferably, the pancreas cells according to the invention are recovered from a foetal canine pancreas removed at days 40 to 55 post conception. Advantageously, the pancreas cells according to the invention are recovered from a foetal canine pancreas removed at days 40 to 46 post conception. In a preferred embodiment, the pancreas cells according to the invention are recovered from a foetal canine pancreas removed at days 45 post conception. Indeed, the inventors have shown that the yield in obtaining the pancreatic beta cells using the method of the invention is high when using foetal canine pancreas removed at days 40 to 60 post conception and is particularly excellent when using foetal canine pancreas removed at days 40 to 46 post conception.

The pancreas cells according to the invention can be recovered by surgery from at least one foetal canine pancreas. The pancreas cells according to the invention can be recovered from the whole foetal canine pancreas or only a portion of said pancreas. Preferably, the pancreas cells according to the invention can be recovered from a portion of the right lobe or a portion of the head of a foetal canine pancreas. Yet preferably, the pancreas cells according to the invention can be recovered from the entire right lobe or the entire head of a foetal canine pancreas. Indeed, the inventors have shown that the yield of pancreatic beta cells using the method of the invention is particularly high when using the right lobe (also named head) of the canine pancreas, or a portion thereof. Indeed, the inventors have shown for the first time that the beta cells are more represented in the right lobe or head of the canine pancreas (Bricout-Neveu et al., 2017).

Thus, such a method could not be implemented so far because the portion of canine pancreas to use and the appropriate stage of development of the collected canine foetus were not known.

In one embodiment, the pancreatic tissue has been frozen after being harvested. In another embodiment, the pancreatic tissue used in the method of the invention is fresh. Thus, according to that specific embodiment, the method of the invention comprises a step of harvesting the pancreatic tissue prior to step a).

In one embodiment, the method of the invention comprises a further step of dissociating immature canine pancreatic tissue with collagenase prior to step a) in order to obtain canine pancreas cells.

By "collagenase", it is herein referred to an enzyme belonging to the matrix metalloproteinase (MMP) family which is capable of breaking the peptide bonds in collagen. A collagenase according to the invention can be either of bacterial or animal origin. Bacterial collagenases differ from vertebrate collagenases in that they exhibit broader substrate specificity. Unlike animal collagenases, bacterial collagenase can attack almost all collagen types, and is able to make multiple cleavages within triple helical regions. Preferably, the collagenase of the invention is a bacterial enzyme; more preferably, it is an enzyme secreted by the anaerobic bacteria *Clostridium histolyticum*. In a preferred embodiment, the collagenase used in the invention is selected from the group consisting of collagenases Type I-S, Type IA, Type IA-S, Type II, Type II-S, Type IV, Type IV-S, Type V, Type V-S, Type VIII, Type XI and Type XI-S. In the most preferred embodiment, the collagenase of the invention is collagenase XI.

The concentration of the collagenase used to obtain canine pancreas cells in the method of the invention is preferably inferior or equal to 5 mg/mL; more preferably, to 4 mg/mL; even more preferably, to 3 mg/mL; still more preferably, to 2 mg/mL; yet even more preferably, to 1 mg/mL. In the most preferred embodiment, said collagenase is used at 1 mg/mL. According to the invention, immature canine pancreatic tissue is dissociated with collagenase for at least 10 minutes; preferably for at least 15 minutes; more preferably at least 20 minutes; even more preferably at least 25 minutes; still more preferably at least 30 minutes; most preferably for 30 minutes at about 37° C. For dissociation to occur, the above-mentioned pancreatic tissues are preferably suspended in an appropriate medium comprising PBS+20% FCS.

By "insulin promoter", it is herein referred to the genomic region containing the regulatory nucleic acid sequences involved in the regulation of the insulin gene expression. In a preferred embodiment, the insulin promoter used in the invention is a murine insulin promoter. Preferably, insulin promoter used in the invention is the rat insulin promoter. Even more preferably, said rat insulin promoter is the promoter described in Castaing et al., 2005.

Transduction of the immature canine pancreas cells obtained from the dissociation of the pancreatic tissues with lentiviral vectors is carried out according to the methods known to the person of skills in the art (see e.g. Russ et al., 2008 and Khalfallah et al., 2009, and references therein). Lentiviral vectors are vectors derived from a lentivirus such as HIV1. They are able to transduce non-dividing as well as dividing cells and sustain expression of heterologous nucleic acid sequences in several target tissues in vivo, including brain, liver, muscle, and hematopoietic stem cells. A great number of lentiviral vectors are already known to the person of skills in the art; any one of these vectors can be used in the context of the present invention, provided that they express at least the SV40 Large T antigen and/or hTERT, under the control of the insulin promoter. The person of skills in the art is directed to Russ et al., 2008 and Khalfallah et al., 2009 where examples of such lentiviral vectors have been described It may be advantageous to de-immortalize the immature canine beta cells of the invention in certain conditions. For example, if administration of the said cells to a patient is contemplated, it is safer to remove the oncogenes carried by the vectors. Lentiviral vectors can thus be constructed to allow reversible or conditional immortalization, so that at least one Lox P site may be introduced. More preferably, the vectors according to the invention are constructed so that the SV40 LargeT and/or the hTERT transgenes are located within two Lox P site. Said transgenes are removed by expressing the Cre recombinase in the beta cells. For example, the cells obtainable by the above method are transduced by a vector or plasmid expressing a Cre recombinase and reversion occurs. Of course, the skilled in the art may choose to use the FRT/FLP system to remove said transgenes. Methods for reverting immortalized cells are described in WO 01/38548.

In a particular embodiment, the lentiviral vector expressing SV40 LargeT and the lentiviral vector expressing hTERT further comprise a LoxP or a FRT site, provided that site specific recombination sites are different in both vectors.

A negative selection step can also be performed after the action of the Cre or FLP recombinase. This further step allows selecting only the cells in which the immortalization genes SV40 LargeT and hTERT, as well as the antibiotic resistance gene, have been removed. These cells can be frozen, stored and optionally encapsulated, until they are transplanted into diabetic canine animals.

The negative selection marker gene can be, for example, the HSV-TK gene and the selective agent acyclovir-ganciclovir. Or the negative selection markers are the hypoxanthine phosphoribosyl transferase (HPRT) gene and the guanine-phosphoribosyl-transferase (Gpt) gene and the selective agent is the 6-thioguanine. Or the negative selection marker is the cytosine deaminase gene and the selective agent is the 5-fluoro-cytosine. Thus, in a preferred embodiment, the said negative marker gene is selected from the group constituted by the HSV-TK gene, the hypoxanthine phosphoribosyl transferase (HPRT) gene, the guanine-phosphoribosyl-transferase (Gpt) gene, and the cytosine deaminase gene. Other examples of negative selection marker proteins are the viral and bacterial toxins such as the diphteric toxin A (DTA). These negative selection genes and agents and their use are well known to the person of skills in the art and need not be further detailed here.

The transduced cells are then introduced into at least one kidney capsule of severe compromised immunodeficiency (scid) animals. A scid animal is an animal lacking T and B lymphocytes and failing to generate either humoral or cell mediated immunity. The scid non-human animal as referred herein can be selected among bovines, porcines, horses, sheep, goats, primates excepted humans, rodents such as mice, rats, hamsters. Said scid non-human animal can carry at least one other type of mutation leading to immunodeficiency. Said scid non-human animal can be a non-obese diabetic/severe combined immunodeficiency (NOD/scid) animal. A NOD/scid animal is an animal lacking T and B lymphocytes, which thus fails to generate either humoral or cell-mediated immunity.

In a preferred embodiment, the NOD/scid animal used in the method of the invention is a mouse. NOD/scid mice are known in the literature and are commercially available from suppliers such as Charles River or Jackson Laboratory. Preferably the NOD/scid mouse used in the method of the invention is of any age of development, preferably sufficiently old so that a graft into the kidney capsule can be performed. Preferably, the NOD/scid mice are about of the 2 to 15 weeks of development, more preferably to 6 to 8 weeks of development.

The inventors have shown for the first time that a canine foetal pancreas normally grows and matures when transplanted under the kidney capsule of scid mice. Moreover, the inventors have shown for the first time that canine insulinoma can be obtained in mice transplanted with immature canine pancreas cell according to the step c) of the method of the invention.

Optionally, the cells are further transduced at step a) with another lentiviral vector expressing an antibiotic resistance gene under the control of the insulin promoter. The antibiotic resistance gene is selected in the group consisting of hygromycin resistance gene, neomycin resistance genes, tetracycline resistance gene, ampicillin resistance gene, kanamycin resistance gene, phleomycin resistance gene, bleomycin resistance gene, geneticin resistance gene, carbenicillin resistance gene, chloramphenicol resistance gene, puromycin resistance gene, blasticidin-S-deaminase gene. In a preferred embodiment, said antibiotic resistance gene is a neomycin resistance gene. In this case, the selective agent is G418.

A method for obtaining human pancreatic cells is disclosed in Ravassard et al. (2011) and WO 2008/102000. However, this method does not allow obtaining and identifying mice carrying canine insulinoma and canine pancreatic beta cells. These publications contain no information regarding dogs and the development of canine pancreas, notably regarding the apparition of insulin-producing cells. Moreover, whereas expression of human insulin confers hypoglycaemia in scid mice, it is not the case with canine insulin. It is therefore not possible to screen scid mice having developed functional canine insulinomas by assaying their glycaemia. Importantly, the inventors were the first to show that canine insulinoma can be detected in the transplanted mice by assaying canine-specific insulin in the mice, allowing for selection of the successfully transplanted mice. Thus, in one embodiment, non-human animals having developed insulinoma-like structures having differentiated to insulin-producing pancreatic cells are selected by measuring the canine-specific insulin level in the non-human animals.

Methods for measuring and/or determining the level of canine-specific insulin are generally known to those skilled in the art and has routinely relied on methods developed to measure human insulin. Methods for measuring and/or determining the level of canine insulin include, for example mass spectrometry, biochemical tests, including immunological tests such as, for example, traditional immunological detection tests (enzyme-linked immunosorbent assay or ELISAs and ELISPOT assays), or such as, for example, immunological tests employing techniques involving transfer of proteins on a support, such as the slot blot (also called dot blot) or the western blot. It is possible, for example, to employ protein microarrays, antibody microarrays or tissue microarrays coupled with immunohistochemistry. Among other techniques that can be used are BRET or FRET techniques, methods of microscopy or histochemistry, including in particular methods of confocal microscopy and electron microscopy, methods based on the use of one or more excitation wavelengths and a suitable optical method, such as an electrochemical method (voltammetry and amperometry), atomic force microscopy, and methods of radio frequency, such as multipolar resonance spectroscopy, confocal and non-confocal, detection of fluorescence, luminescence, chemiluminescence, absorbance, reflectance, transmittance, and birefringence or refraction index (for example, by surface plasmon resonance, by ellipsometry, by a resonant mirror method, etc.), flow cytometry, by radio-isotope or magnetic resonance imaging, analysis by polyacrylamide gel electrophoresis (SDS-PAGE); by HPLC-mass spectrophotometry, by liquid chromatography/mass spectrophotometry/mass spectrometry (LC-MS/MS). All these techniques are well-known to the skilled person and it is not necessary to detail them herein.

Thus, in one embodiment, the method of the invention further comprises a step of measuring the level of canine-specific insulin prior to step d) in order to select non-human animals having developed insulinoma-like structures having differentiated to insulin-producing pancreatic cells. In one embodiment, the level of canine-specific insulin is measured using a canine-specific insulin antibody. Such antibodies are commercially available. Advantageously, the canine-specific insulin antibody is comprised in a kit. Preferably, the level of canine-specific insulin is measured by ELISA. Advantageously the level of canine-specific insulin is measured by ELISA using a canine-specific ELISA kit comprising a canine-specific insulin antibody. Canine-specific ELISA kits may further include antibodies, calibrators, buffer, and analytic range optimized for canine insulin.

The above-defined method includes collecting the canine functional pancreatic beta cells obtained at step g) which form a homogenous cell population. The cell population can further be cultured in vitro to establish a canine functional beta cell line. At this stage, the cells derived from the successive sub-grafts contained the SV40 LargeT and/or the hTERT and the antibiotic resistance transgenes. Thus, the cell lines obtainable by the above method are immortalized and depending on the end point they may or may not be reversed (de-immortalized). In particular, de-immortalization can be useful when a therapeutic use of the cells of the invention is contemplated.

The above method to prepare canine functional pancreatic beta cells is particularly useful for testing and screening candidate medicaments for treating canine diabetes in vivo after graft in non-human animals, such as mice or rats, or in vitro.

In this regard, and in one specific embodiment, the above method can be put to practice to prepare large amount of canine functional pancreatic beta cells for testing and screening purposes as well as for in vitro diagnosis of canine diabetes allowing classification of diabetic animals in type 1 diabetes or other types of diabetes. Here, the cells may be de-immortalized. On the contrary, with the above method, steps f), g) and h) can be repeated as many times as necessary to obtain large amount of insulinoma or isolated canine beta cells thereof and these cells may further be amplified in culture in vitro ad infinitum. Cross section of beta cell tumours, cells derived thereof or protein extract from these cells can be bound or adsorbed to a solid support (for example polylysine coated plates) and reacted with the plasma serum of canine animals. After incubation, the serum is washed out and the presence or absence of autoantibodies against different surface antigens specific to autoimmunity associated with diabetes is revealed (for example by means of labelled anti-canine Ig).

Therefore, in a second aspect, the invention is aimed at canine beta cell tumours or insulinomas, or canine pancreatic beta cells obtainable by the above-described method. These canine beta cell tumours or canine pancreatic beta cells display at least one of the following features:
expression of canine-specific insulin and
transcriptional factor Pdx positive.

Advantageously, said canine beta cell tumours or canine pancreatic beta cells further display at least one of the following features:
Carboxypeptidase-A negative
transcription factor MafA positive
proconvertase Pcsk1 positive
expression of Glucose transporter Glut2
expression of Kcnj11 and Abcc8 coding for subunits of the potassium channel
expression of zinc transporter Znt8 (Slc30a8).

Canine beta cell tumours or canine pancreatic beta cells as defined above are also positive to reaction with anti-insulin, anti-GAD and/or anti-IA2 antibodies and can be maintained and grown in culture in a medium free of serum and on Matrigel or on fibronectin coated wells. Indeed, the inventors were the first to show that the canine beta cell tumours or canine pancreatic beta cells, grown and maintained in such medium, are capable of stably, efficiently and homogenously producing canine insulin. Thus, the invention also contemplates a cell culture comprising the above-described canine pancreatic beta cells in culture in a medium free of serum comprising Matrigel or fibronectin. This cell culture allows to expand and to establish immortalized canine pancreatic beta cell lines.

Moreover, the cell lines obtainable by the above-described method may be de-immortalized, so that they can be used for example for testing and screening purposes as well as for in vitro diagnosis of canine diabetes allowing classification of diabetic animals in type 1 diabetes or other types of diabetes.

By "diabetes", it is herein referred to a chronic, often debilitating and sometimes fatal disease, in which the body either cannot produce insulin or cannot properly use the insulin it produces. A canine type 1 diabetes according to the invention is a diabetes resulting from autoimmune destruction of beta cells. As used herein, "other types of diabetes in dogs" or "other types of canine diabetes" refer to canine diabetes which are not of the type 1.

The above described method to prepare canine functional pancreatic beta cells is particularly useful for testing and screening candidate medicaments for treating canine diabetes in vivo after graft in non-human animals, such as mice or rats, or in vitro. Specifically, the invention relates to a method for testing and screening candidate medicaments for treating canine diabetes, said method comprising the step of administering a candidate medicament to a non-human animal grafted with the canine pancreatic cells of the invention. In a more specific embodiment, the method comprises prior steps of obtaining said beta cells according to the methods described above, and grafting said cells into the said non-human animal. Said non-human animal is preferably a scid non-human animal, as described above.

The present invention also relates to a method of in vitro diagnosis of canine diabetes. Cross section of beta cell tumours, cells derived thereof or protein extract from these cells can be bound or adsorbed to a solid support (for example polylysine coated plates) and reacted with the plasma serum of animals. After incubation, the serum is washed out and the presence or absence of auto-antibodies against different surface antigens specific to autoimmunity associated with canine diabetes is revealed (for example by means of labelled anti-human Ig).

Thus, in one embodiment, the invention relates to a method of in vitro diagnosis of canine diabetes comprising linking or adsorbing canine beta cell tumours or canine pancreatic beta cells as described above, or protein extract from said cells, to a solid support and reacting with the plasma serum of animals, detecting the presence or absence of auto-antibodies against different surface antigen specific to canine diabetes type 1 or other types of diabetes, such as Islet Cells Antibodies (ICA), selected for example from Insulin auto-antibodies (IAA) and glutamic acid decarboxylase antibodies (GADA).

Preferably, sera from diabetic animal and control animal are added on said tissue sections of said canine beta cell tumours or canine beta cells, and incubated with a labelled anti-canine IgG, such as a fluorescent labelled conjugated anti-canine IgG, in order to reveal the presence or absence of auto-antibodies associated with canine diabetes in the sera of said patient animal. In this embodiment, the presence of auto-antibodies is indicative of canine diabetes.

The presence or absence of auto-antibodies associated with canine diabetes in the sera of said diabetic animal can also be detected by a western blot of a protein extract of said canine beta cell tumours or said canine pancreatic beta cells. In this case, the presence or absence of auto-antibodies associated with canine diabetes in the sera of said diabetic animal is detected with labelled anti canine IgG, such as HRP conjugated anti canine IgG. Alternatively, the presence or absence of auto-antibodies associated with canine diabetes in the sera of said diabetic animal is detected by an ELISA test in which the wells plates are coated with a protein extract of said canine beta cell tumours or said canine pancreatic beta cells. According to this embodiment, said protein extract is incubated with sera from diabetic animal and control animal, and the presence or absence of auto-antibodies associated with canine diabetes in the sera of said diabetic animal is detected with labelled anti canine IgG, such as HRP conjugated anti canine IgG.

In another aspect, a method of in vitro diagnosis of canine diabetes comprises reacting section of beta cell tumours, cells derived thereof or protein extract of these cells obtainable by the method depicted above with the plasma serum of animals, detecting the presence or absence of autoantibodies against different surface antigen specific to canine type 1 diabetes or other types of canine diabetes, such as Islet Cells Antibodies (ICA), or more specific antibodies recently identified like antibodies against Insulin autoantibodies (IAA) and glutamic acid decarboxylase antibodies (GADA) or IA-2 antibodies (IA2A) or specific unknown antibodies. The identification of known or new antibodies can be performed by immunoblot or dot-blot for example.

This aspect of the invention provides for the first time a kit that can be prepared at a commercial scale for diagnosing canine diabetes and for classification of diabetes type. More particularly, this kit can be used to detect specific canine autoantibodies such as Islet Cells Antibodies (ICA) selected from Insulin autoantibodies (IAA) and glutamic acid decarboxylase antibodies (GADA). Indeed, these antigens are expressed at the surface of the beta cell tumours or cells derived thereof obtainable according to the above method. Thus, embraced herein is a diagnostic kit for canine diabetes, said kit comprising canine beta cell tumours or canine functional pancreatic beta cells obtainable by the above method, or proteins extract there from, optionally bond or adsorbed to a solid support.

In another embodiment, the cells as described above are cultured in vitro and canine pancreatic beta cell lines are established for screening compounds capable of modulating insulin secretion. The present invention thus also provides a method for screening compounds capable of modulating insulin secretion, said method comprising the steps of: a) contacting the canine pancreatic beta cells of the invention with a test compound, and b) detecting insulin secretion and measuring the level of insulin secretion. Insulin secretion can be detected by any of the means known to the person of skills in the art, as detailed in e.g. the experimental examples below, in Ravassard et al, and in WO 2008/102000. According to a preferred embodiment, the screening method of the invention comprises a step of comparing the level of secreted insulin obtained in step b) with at least one control level. Said control level corresponds to the level of insulin produced by a cell line which is known to secrete insulin. Alternatively, said control level corresponds to the level of insulin produced by a cell line which is known not to produce any insulin. In a further preferred embodiment, the secreted insulin level of step b) is compared with two control levels, one corresponding to the level of insulin produced by a cell line which is known to secrete insulin and the other one corresponds to the level of insulin produced by a cell line which is known not to secrete insulin. In yet another preferred embodiment, the screening method of the invention comprises a prior step of obtaining the canine pancreatic beta cell line according to the method for preparing canine pancreatic beta cells described above.

In still another embodiment, the method for preparing canine pancreatic beta cells as described above is directed to the establishment of master cell banks for cell therapy of canine diabetes. Here, said method further includes de-immortalizing the cells. Said de-immortalization of the cells includes a step of removing the SV40 LargeT and the hTERT transgene from the lentiviral vectors. Preferably the transgenes are excised by site-specific recombination with a site-specific recombinase such as Cre or FLP, as described above.

In still another embodiment, the invention relates to the canine beta cell tumours and isolated cells thereof obtainable by the method for preparing canine pancreatic beta cells as described above. As explained, both immortalized and de-immortalized are encompassed herein.

The invention also concerns the use of said cells for testing or screening candidate medicaments for the treatment of canine diabetes, for in vitro diagnosis of canine diabetes as explained above and for cell therapy of canine diabetes.

The present invention also provides a method of regenerating canine pancreas function in an individual animal afflicted with canine diabetes, the method comprising a step of administrating an effective amount of the canine functional pancreatic cells as defined above, said cells being reverted to a primary beta cell phenotype, into said animal. In a preferred embodiment, said cells are transplanted within said animal. In another preferred embodiment, said method of regenerating pancreas function comprises a prior step of obtaining the said canine pancreatic beta cells by the method described above.

The invention also relates to a pharmaceutical composition comprising a pharmaceutical acceptable carrier and an effective amount of the canine functional pancreatic cells as defined above, said cells being optionally encapsulated.

An "effective amount" is an amount sufficient to effect beneficial or desired clinical results. An effective amount, for example from $10^5$ to $10^9$ cells, can be administered in one or more applications, although it is preferable that one administration will suffice. For purposes of this invention, an effective amount of stem cells precursors of pancreatic beta cells is an amount that is sufficient to produce differentiated pancreatic cells which are able to restore one or more of the functions of the pancreas. It is contemplated that a restoration can occur quickly by the introduction of relatively large numbers of pancreas cells, for example greater than $10^9$ cells. In addition, it is also contemplated that when fewer pancreatic cells are introduced, function will be restored when the pancreas cell or cells are allowed to proliferate in vivo. Thus, an "effective amount" of pancreatic cells can be obtained by allowing as few as one pancreas cell sufficient time to regenerate all or part of a pancreas. Preferably, an effective amount administered to the individual is greater than about $10^1$ pancreas cells, preferably between about $10^2$ and about $10^{15}$ pancreas cells and even more preferably, between about $10^3$ and about $10^{12}$ pancreas cells. In terms of treatment, an "effective amount" of pancreatic cells is the amount which is able to ameliorate, palliate, stabilize, reverse, slow or delay the progression of pancreas disease, such as diabetics.

As used herein, "pharmaceutically acceptable carrier" includes any and all solvents, buffers, salt solutions, dispersion media, coatings, antibacterial and antifungal agents, isotonic and absorption delaying agents, and the like that are physiologically compatible. The type of carrier can be selected based upon the intended route of administration. In various embodiments, the carrier is suitable for intravenous, intraperitoneal, subcutaneous, intramuscular, topical, transdermal or oral administration. Pharmaceutically acceptable carriers include sterile aqueous solutions or dispersions and sterile powders for the extemporaneous preparation of sterile injectable solutions or dispersion. The use of media and agents for pharmaceutically active substances is well known in the art. A typical pharmaceutical composition for intravenous infusion could be made up to contain 250 ml of sterile Ringer's solution, and 100 mg of the combination. Actual methods for preparing parenterally administrable compounds will be known or apparent to those skilled in the art and are described in more detail in for example, Remington's Pharmaceutical Science, 17th ed., Mack Publishing Company, Easton, Pa. (1985), and the $18^{th}$ and $19^{th}$ editions thereof, which are incorporated herein by reference.

Methods of introducing cells into canine animals are well known to those of skills in the art and include, but are not limited to, injection, intravenous or parenteral administration. Single, multiple, continuous or intermittent administration can be effected. The canine beta cells of the invention can thus be introduced into any of several different sites, including but not limited to the pancreas, the abdominal cavity, the kidney, the liver, the portal vein or the spleen. Preferably, said beta cells are deposited in the pancreas of the animal.

The canine pancreatic beta cells of the invention can be useful for regenerating pancreatic functions. Said cells can also be administered to an animal suffering from a pancreatic disorder in order to treat said disorder. Thus, the present invention also contemplates a method for treating a canine pancreatic disorder with canine pancreatic beta cells obtained by the method of the invention, comprising the administration of the said canine pancreatic beta cells to an animal in need thereof. According to a preferred embodiment, the treatment method of the invention comprises a prior step of obtaining the said canine pancreatic beta cells from a canine pancreatic tissue. In a further preferred embodiment, the canine pancreatic tissue is obtained from said animal in need of a treatment.

It is thus another aspect of the present invention to provide canine pancreatic cells of the invention as a medicament. More precisely, the present invention relates to the use of canine pancreatic beta cells of the invention for preparing a medicament to treat a canine pancreatic disorder. Yet another aspect of the invention relates to the canine pancreatic beta cells of the invention for use in treating a canine pancreatic disorder.

A canine pancreatic disorder according to the invention is diabetes, hypoglycaemia, or any pathology associated with a dysfunction of the digestive enzymes. Preferably, a canine pancreatic disorder is insulin-dependent diabetes (T1D).

FIGURE LEGENDS

FIG. 1: Dog pancreas development and endocrine cell distribution during the third quarter of foetal development Immunostaining of endocrine markers, insulin (light grey) and glucagon (white) on 4 μm paraffin sections on either dissected mid gut tube for dog embryos of 30 and 33 days pc (E-30, E-33) or dissected pancreas from embryos at E-45. The left lanes present large field images of the immunostaining. For each developmental stage higher magnification of the insert marked with a dotted line is presented on the right lanes. Nuclei were stained with DAPI (dark grey). Large field scale bars=100 μm, Insert scale bars=20 μm.

Figure 2:
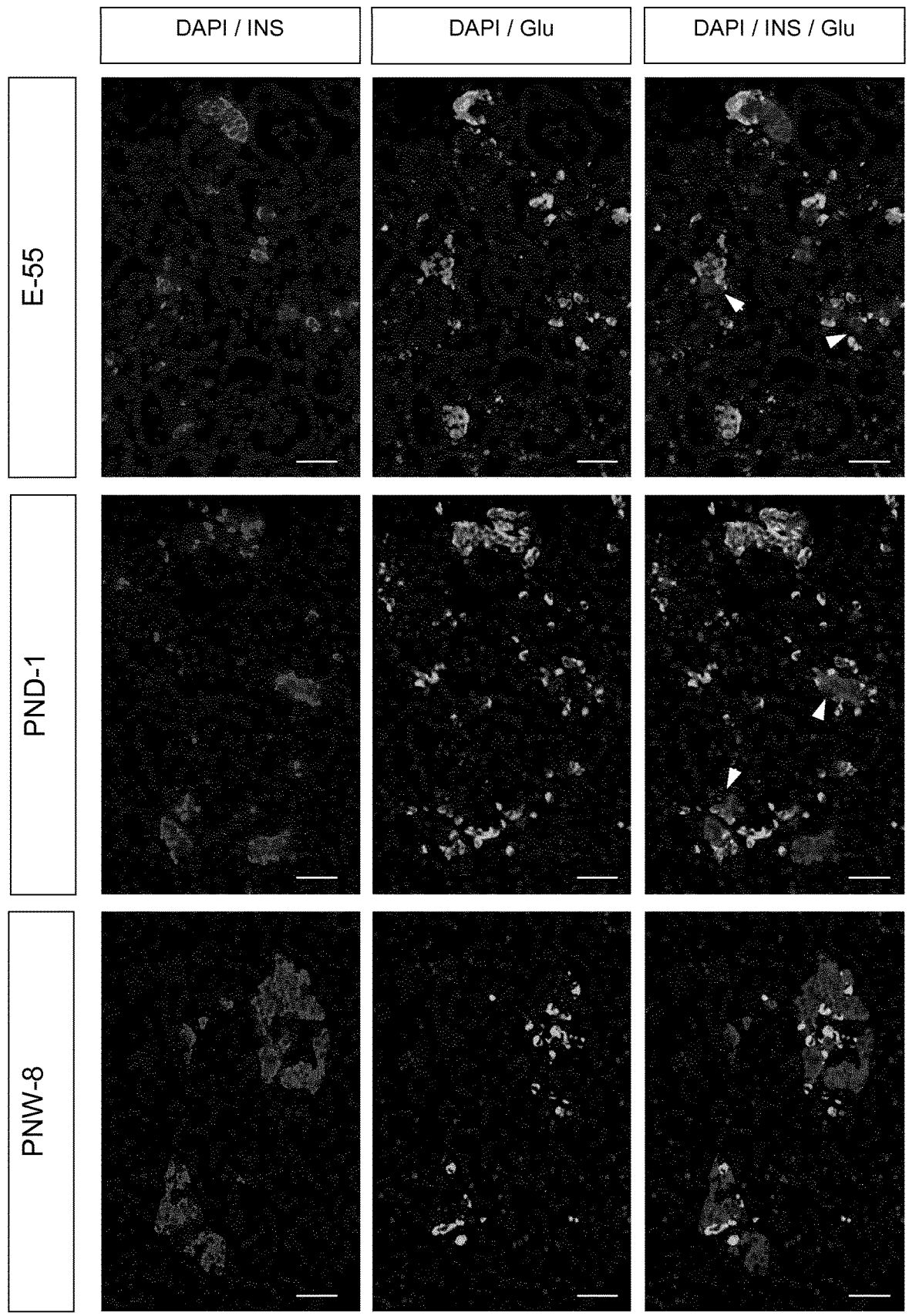

FIG. 2: Dog pancreas development and endocrine cell distribution during the perinatal period and before weening Immunostaining of endocrine markers, insulin (light grey) and glucagon (white) on 5 μm paraffin sections of dog pancreases obtained from embryos of 55 days pc (E-55), from new-borns at day 1 postnatal (PND1) and from young's before weaning at week 8 (PNW8). Both insulin and glucagon staining are presented separately in the left and middle panel respectively. Merge immunostaining is presented on the right panel. Nuclei were stained with DAPI (dark grey). Arrows point to cell clusters containing both insulin and glucagon with the morphology of islet like structures. Scale bars=20 μm.

Figure 3:
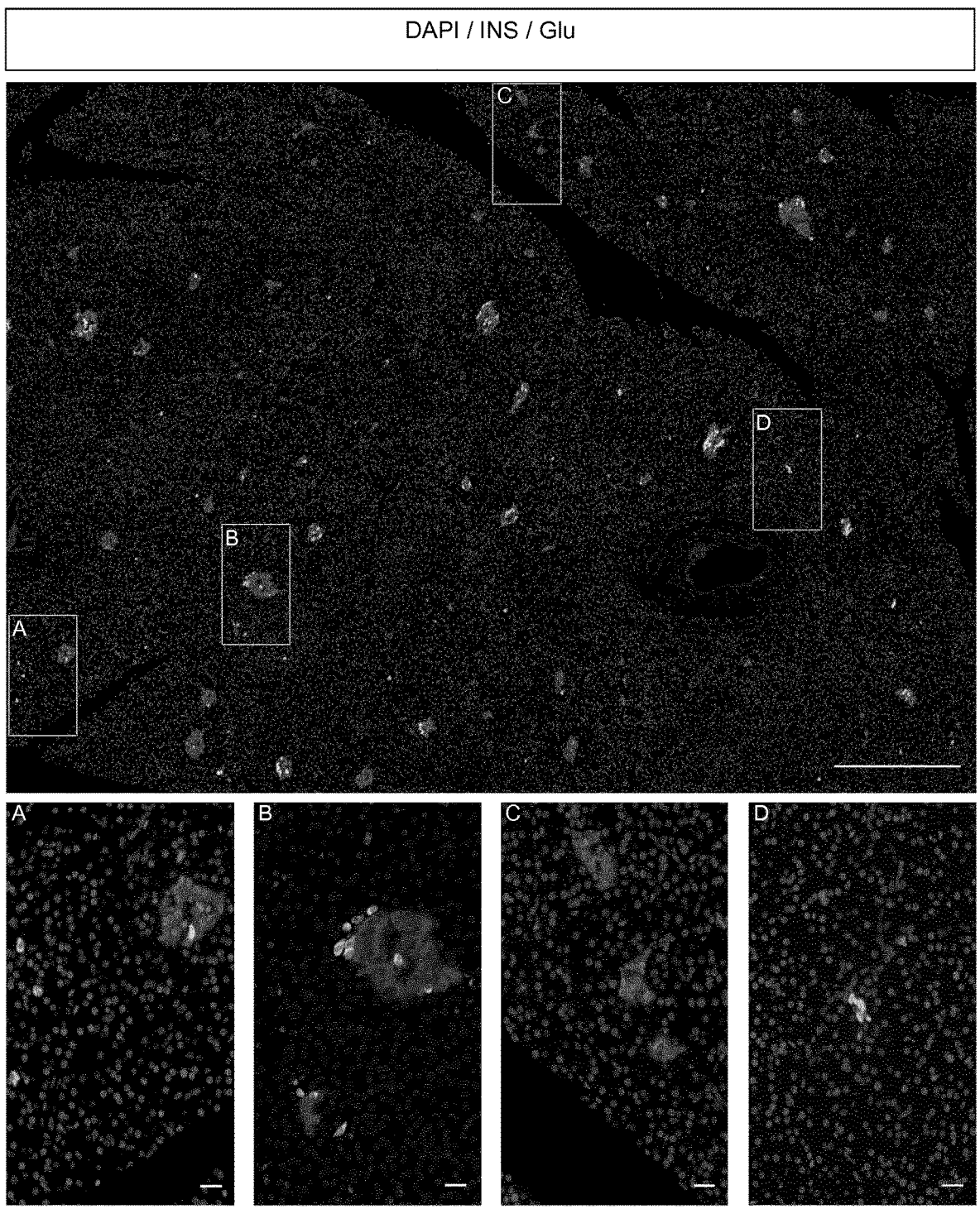

FIG. 3: Endocrine cells in adult dog pancreas are organized as islets

Immunostaining of endocrine markers, insulin (light grey) and glucagon (white) on 5 μm paraffin sections of dog left lobe of the pancreas. Top panel present large field images of the immunostaining. Four inserts marked with a dotted line (A to D) were magnified and are presented in the bottom lane. Nuclei were stained with DAPI (dark grey). Large field scale bars=500 μm, Insert scale bars=20 μm.

Figure 4:
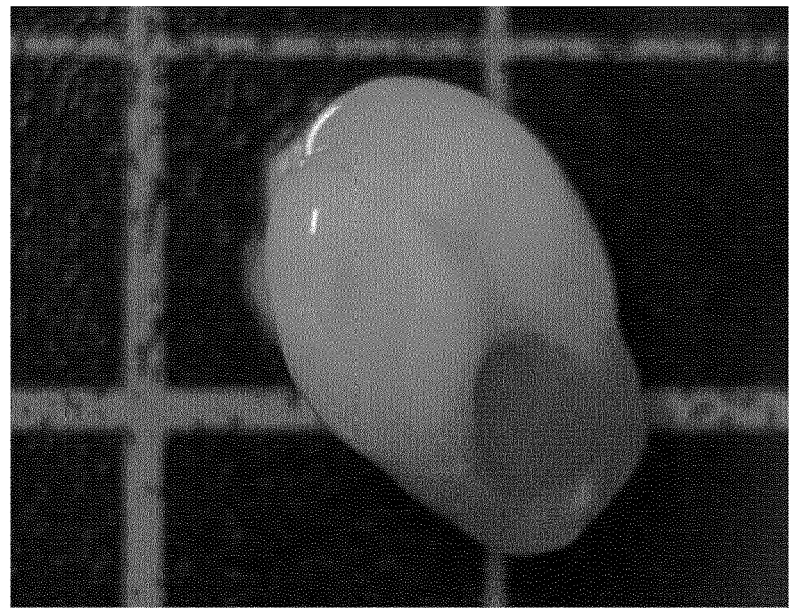
Figure 4:
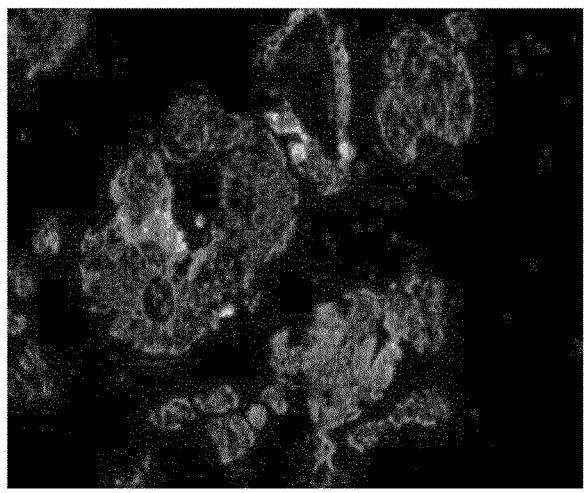
Figure 4:
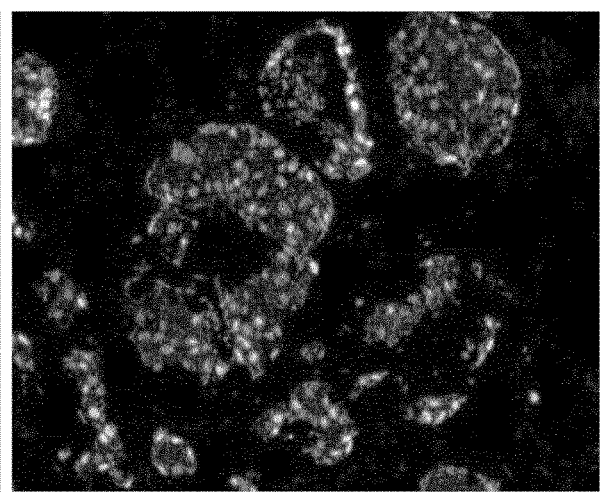

FIG. 4: Grafts of immature canine pancreatic tissue in a scid mouse results in the development of a fully mature pancreas organ containing both endocrine and exocrine tissue A) A pancreas obtained from a foetus at 42 days post conception was grafted under the kidney capsule of a scid mouse. A tumour developed after 2 months. B) Immunostaining of endocrine markers, insulin (light grey) and glucagon (white). C) Immunostaining of endocrine marker insulin (light grey) and transcription factor PDX (white).

Figure 5:
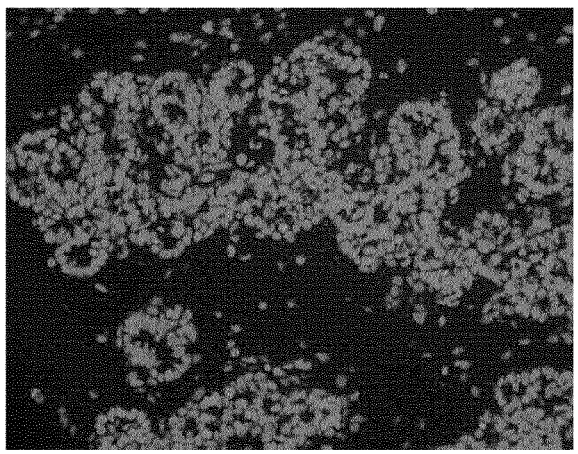
Figure 5:
Figure 5:
Figure 5:
Figure 5:
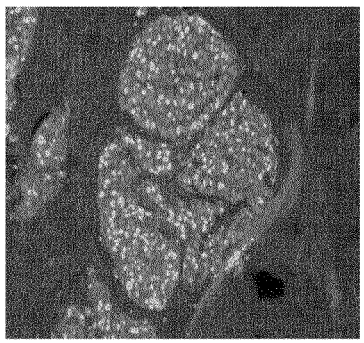
Figure 5:

FIG. 5: Insulinoma obtained after transduction and grafting of immature canine pancreatic tissue in a scid mice A dog foetal pancreas at 45 days post conception was harvested and transduced with LargeT gene (oncogene SV40). A) Hoechst staining (dark grey) and immunostaining of endocrine marker insulin (light grey) of mouse pancreas before and after transplant. After transplantation tumour (insulinoma) has formed. B) Grafted mouse pancreas two months after transplant. C) Immunostaining of endocrine marker insulin (light grey) and LargeT (white) of insulinoma removed from the grafted mouse pancreas two months after transplant. LargeT expression colocalises with insulin secretion.

Figure 6:
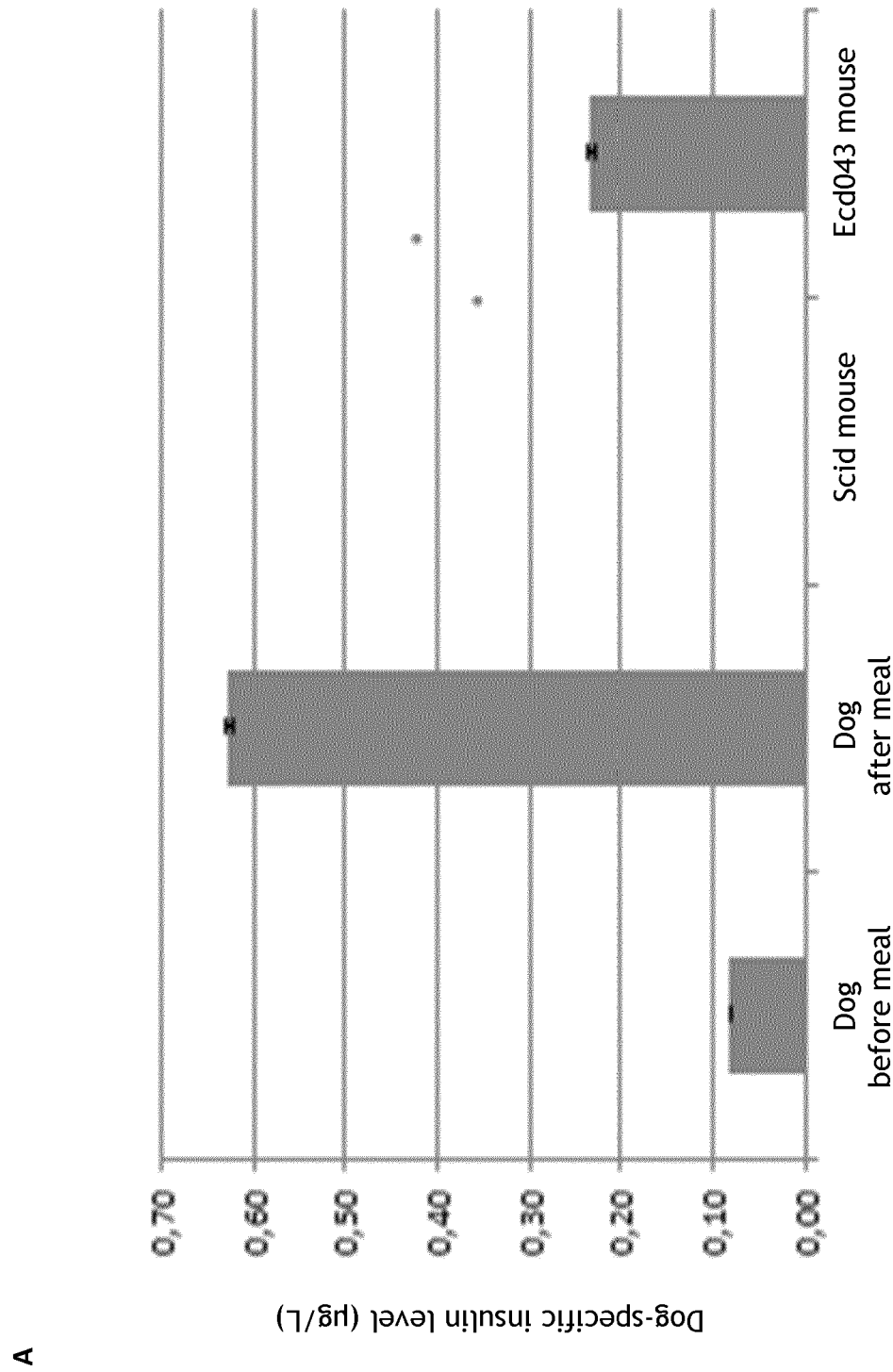
Figure 6:
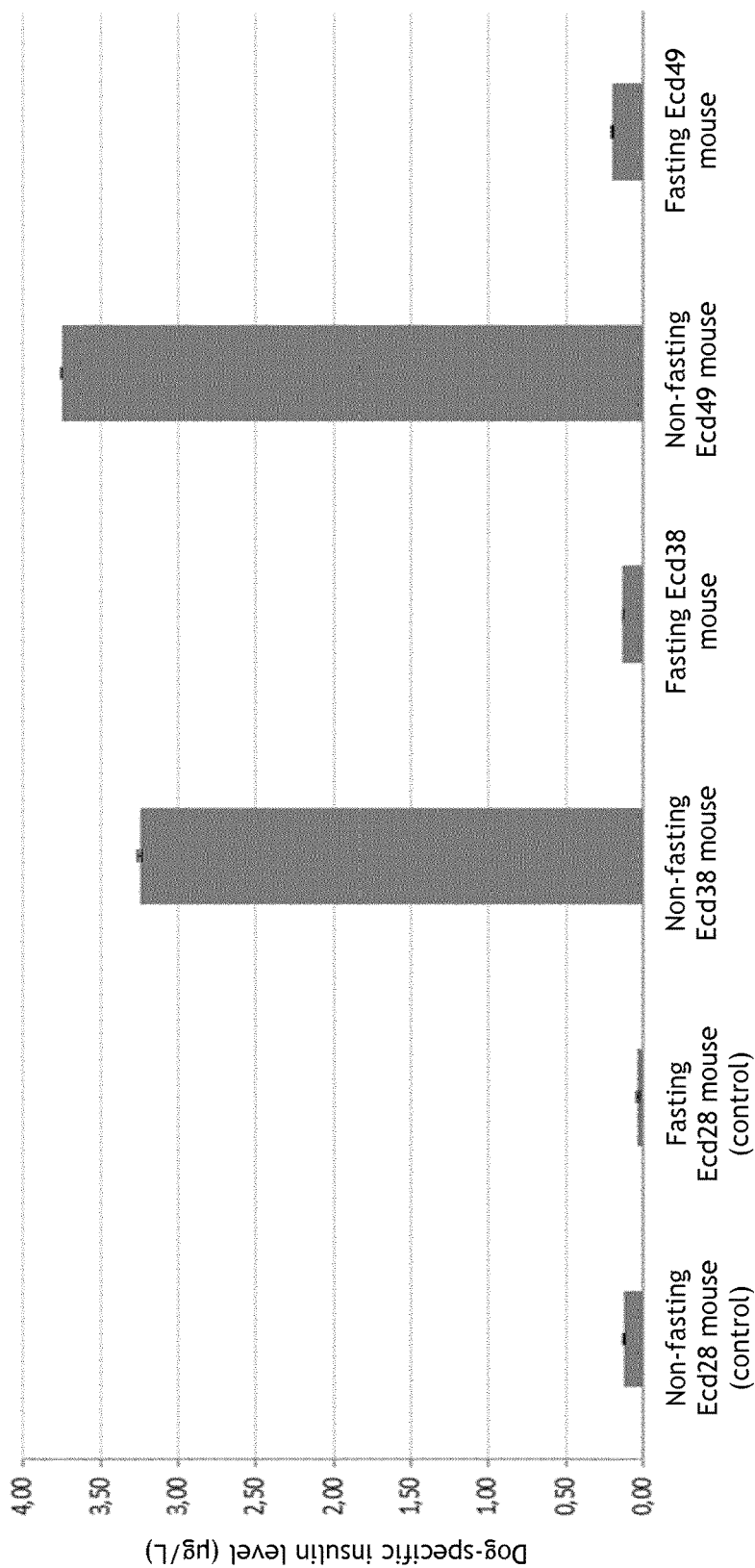

FIG. 6: Mice grafted with transduced canine pancreatic cells develop an insulinoma secreting regulated dog-specific insulin A) Comparative dog-specific insulin plasma assay in an adult dog before versus after feeding, and in a non-grafted mouse versus a canine beta cells grafted mouse. Assaying dog-specific insulin in the mouse grafted with a dog insulinoma predicts the presence of the tumour. B) Comparative dog-specific insulin assay in transplanted mice, which have been fasting (fasting) or normally fed. Dog-specific insulin secretion is regulated by glycaemia levels in transplanted mice.

Figure 7:
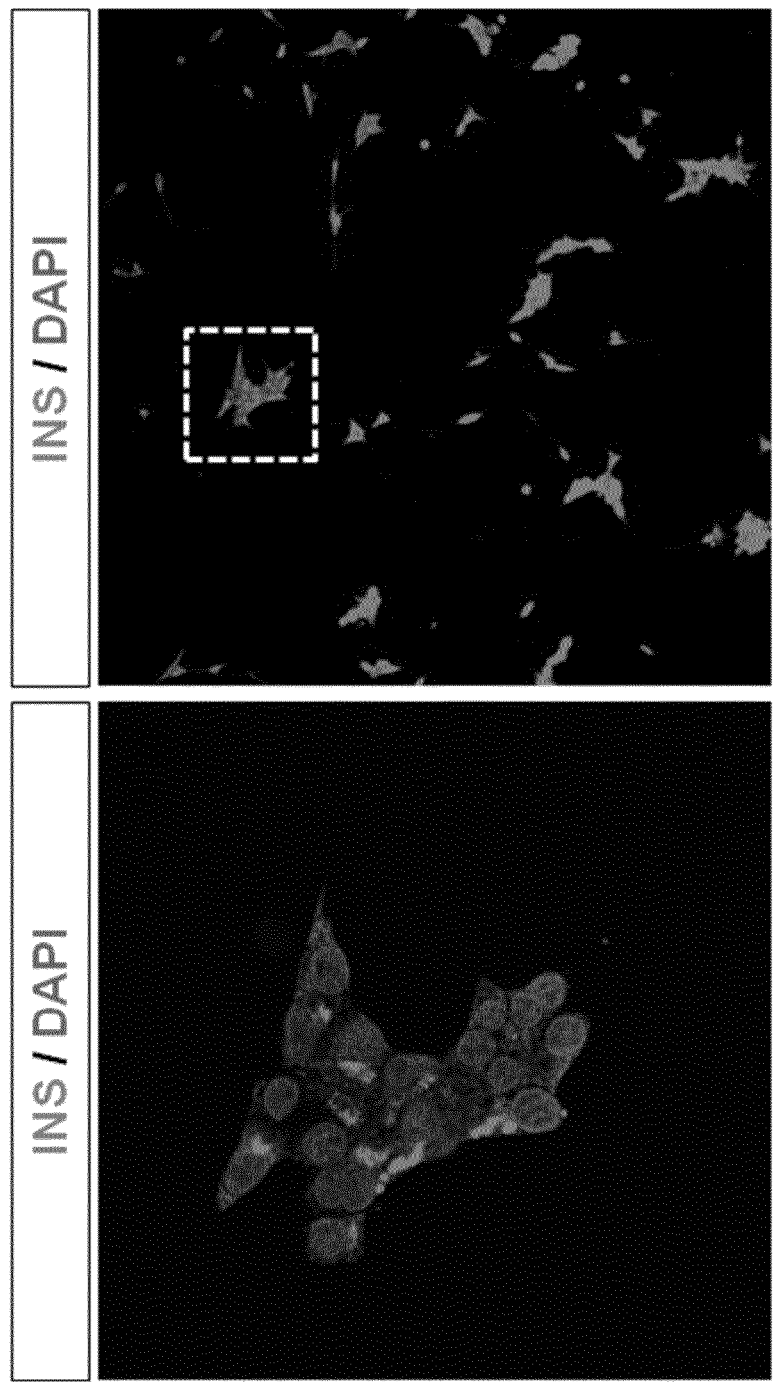

FIG. 7: The dog beta cell lines are functional and produce dog insulin

Immunostaining of a dog beta cell line generated from insulinoma secreting dog-specific insulin. Cells were stained with an anti-insulin antibody (light grey) and the nucleus were stained with DAPI (dark grey). The cells were observed by confocal microscopy. The bottom panel shows a close-up on one of these cells (indicated by an insert marked with a dotted line on the top panel).

EXAMPLES

A) Material and Methods

A.1. Source of Canine Pancreatic Tissue and Collection Procedure

As shown in Table 1, six developmental stages of the foetal dog pancreas were selected, at day 30, 33, 36, 40, 45 and 55 days post conception (pc). The study focused on one single strain of Beagle dogs, a strain raised in the housing facilities of Maison-Alfort Veterinary School except for the foetal pancreas studied at 55 days pc. The mother of this foetus obtained at 55 pc was not raised in the Veterinary school of and its foetus obtained at 55 pc was of an unknown breed. Its mother's stature was equivalent to a beagle.

All foetal samples were obtained by elective caesarean section. The foetal age was determined according to the ovulation identified by the plasma progesterone surge (except for the 55 days old foetus).

In addition, pancreases were also obtained from two Beagle dogs that died during hospitalization either during the early neonatal period at 1 day post-delivery or at weaning at 8 weeks. A pancreas from 1 adult dog was also studied. This sample was obtained from a Labrador euthanized for a progressive and severely incapacitating neuromuscular disorder.

The morphology of a Beagle dog pancreas obtained at foetal stage 46 days pc and at 1 day post-delivery were compared to the pancreases of a Labrador and a Chow-chow respectively.

All the procedures involving animals were approved by the Ethic Committee of Maison-Alfort Veterinary School A.2. Preparation of Canine Pancreatic Tissue Immediately after surgery, all pancreases were dissected and fixed in 3.7% formaldehyde prior to their embedding in paraffin. For the pancreases at 30 and 33 days pc, the whole mid gut tubes including pancreas and stomach were dissected whereas for later stages the pancreas only was dissected. The pancreatic tissues of the new-born (1 day) and the young dog (8 weeks) were dissected in the hour following the death of the dogs and fixed in a PBS-10% formol solution prior to paraffin embedding. The same procedure was applied to the pancreatic fragment obtained from an adult dog. In that case, the pancreatic sections were sampled from the right lobe.

A. 3. Immunohistochemistry

Paraffin-embedded sections were cut with a thickness of 4 μm for early stages and 5 μm for post-natal and adult stages. Sections were stained with a guinea pig anti-insulin antibody (1/500; A0564, Dako-Cytomation) and rabbit anti-glucagon (1/1000; 20076-Immuno, Euromedex). The secondary antibodies were fluorescein Texas red anti-guinea pig antibody (1/2000; 706-076-148, Jackson and anti-rabbit antibody (1/200; 711-096-152, Jackson Immunoresearch Laboratories, Beckman Coulter). Digital images were captured using an Axio Scan Z1 (Zeiss).

Numbers of slice obtained from each specimen and number of slices analysed are described in Table 1.

TABLE 1

Numbers of slices obtained from each specimen and number of slices that have been analysed.

| Development stages (days post conception) | Breed | Tissues | Number of slices analysed/total number of slices made |
|---|---|---|---|
| 30 days | beagle | Pancreata + stomach | 300/300 |
| 33 days | beagle | Pancreata + stomach | 50/273 |
| 36 days | beagle | Pancreata | 30/295 |
| 40 days | beagle | Pancreata | 50/240 |
| 45 days | beagle | Pancreata | 73/495 |
| 55 days | unknown | Pancreata | 37/168 |
| 1 day postnatal | beagle | Pancreata | 52/268 |
| 8 weeks postnatal | beagle | Pancreata | 42/216 |

The slices that were analysed were selected randomly and are representative of the total tissue.

A.4. DNA Constructs and Recombinant Lentiviral Productions

The lentiviral vectors, pTRIP ΔU3.RIP405-SV40LT loxP and pTRIP ΔU3.RIP405-hTERT loxP, have been constructed by adding a loxP site in the 3'LTR region of the pTrip ΔU3.RIP405-SV40LT/hTERT previously described (Ravassard et al, 2009). Both pTRIP ΔU3 vectors were digested by KpnI and PacI to remove the 3'LTR region. The 3'LTRloxP region of the SIN-RP-LTcDNA-WHV-U3loxP (provided by Bernard Thorens) was amplify by PCR and next digested by KpnI and PacI and then ligated into the two linearized pTrip vectors. The Lentiviral vector stocks were produced by transient transfection of 293T cells by encapsidation of the p8.9 plasmid (ΔVprΔVifΔVpuΔNef), pHCMV-G that encoded the VSV glycoprotein-G and the pTRIP ΔU3 recombinant vector, as previously described (Zufferey et al., 1997). The supernatants were treated with DNAse I (Roche Diagnostic) prior to their ultracentrifugation, and the resultant pellets were re-suspended in PBS, aliquoted, and then frozen at −80° C. until use. The amount of p24 capsid protein was quantified by the HIV-1 p24 antigen ELISA (Beckman Coulter). All transductions were normalized relative to p24 capsid protein quantification.

A.5. Gene Transfer

The pancreatic tissue was cut in 1 mm square pieces in foetal calf serum, treated with collagenase XI (1 mg/ml RPMI) (Sigma-Aldrich) during 30 minutes at 37° C. and next rinsed twice in PBS containing 20% foetal calf serum. New-born pancreases were transduced with pTRIP ΔU3.RIP405-SV40LT loxP as previously described (Castaing et al., 2005; Scharfmann 2008). Briefly, tissues were transduced with a total amount of lentiviral vectors corresponding to 2 μg of p24 capside protein for two hours at 37° C. in 200 μl of DMEM that contained 5.6 mM glucose, 2% bovine serum albumin fraction V (BSA, Roche diagnostics), 50 μM 2-mercaptoethanol, 10 mM nicotinamide (Calbiochem), 5.5 μg/ml transferrin (Sigma-Aldrich), 6.7 ng/ml selenite (Sigma-Aldrich), 100 U/ml penicillin, and 100 μg/ml streptomycin and 10 μg/ml DEAE-dextran. Tissues were then washed twice with medium culture and kept on culture overnight until transplantation into scid mice.

A.6. Animals and Transplantation into Scid Mice

Male scid mice (Harlan) were maintained in isolators. Using a dissecting microscope, pancreases or islets were implanted under the kidney capsule, as previously described (Ravassard et al., 2011). At different time points after transplantation, the mice were sacrificed, the kidney removed, and the graft dissected. All animal studies and protocols were approved by the Veterinary Inspection Office in compliance with the French legislation under agreement number B75-13-03.

A.7. Assay of Dog-Specific Insulin Levels

The levels of dog-specific insulin were assayed using an ELISA kit commercialized by MERCODIA, following the instructions of the manufacturer.

B) Study of Canine Pancreas Development

1—Introduction

The method of the invention allows obtaining canine beta cell lines which can be maintained and expanded in vitro. This is a first step towards developing a cellular therapy of canine diabetes.

In order to identify the most suitable foetal stage to harvest pancreas of the method of the invention, a study of the early morphological development of the canine endocrine pancreas was therefore undertook. This study also accounts for a first step in the description of insulin's role in canine foetal development. The first aim in this work was to determine the phase of the pancreatic development at which the primitive pancreas progresses from hormone negative to hormone positive cells. To this end, insulin and glucagon expression was analysed in dog foetal pancreas, using immunohistochemistry. The second aim was to determine the stage of foetal or early postnatal development at which the highly-organized structure of the islet of Langerhans is formed. Finally, the immuno-histological structure of the endocrine pancreas was studied in adult dogs.

2—Results

The development of the foetal dog pancreas from 30 days post conception (pc; E-30) to 45 days pc (E-45) is shown in FIG. 1. On the left lane from top to bottom the pancreatic epithelium undergoes a marked process of expansion and branching from the dense epithelial bud at Days 30 and 33 localized close to the stomach to a clearly branched epithelium from Day 36 to 45 (FIG. 1, E-30 to E-45). In the branched epithelium both trunk and tips areas can be observed (FIG. 1, E-36 and E-45, arrows).

At 30 and 33 days pc, rare insulin positive beta cells are detected (E-30 and E-33). For the younger pancreases, beta cells were found in only 25% of the examined slices. Insulin positive cells therefore emerge at mid gestation around 30 days of the foetal life. Glucagon cells are much more frequently seen. Both cells are isolated and dispersed throughout the pancreatic bud. By Day 36 (E-36), the number of beta and alpha cells is increasing but glucagon cells predominate. The pancreas epithelium is branched and the endocrine cells are mostly localized within the truncal area. Small clusters of beta or alpha cells can be observed although the majority of endocrine cells are isolated. At 45 days pc (E-45), the endocrine clusters are bigger and in rare clusters both alpha and beta cells can be observed (FIG. 1, arrows). Similar observations were made for various dog breeds. Thus, at the junction of the second third with the last third of gestation (E-36), very few beta cells can be observed. This is in contrast with observations in other species and in particular in humans which revealed that large numbers of beta cells can be observed as soon as the end of the first third of pregnancy. This pattern of pancreas development is thus specific to dogs.

The development of the pancreas at the end of gestation (55 days pc), as well as in one day old pups (PND-1) and 8-week-old pups (PNW-8) is shown in FIG. 2. During the perinatal period (E-55 and PND1) the number of beta cells is increasing compared to earlier stages of development. Alpha and beta cells are localized in clusters and small islets like structures are visible (arrows). Before weaning at week 8 (PNW8), insulin cells predominate over alpha cells and endocrine cells are organized in islets-like clusters (FIG. 2).

The description of a mature adult dog pancreas is shown in FIG. 3. Isolated alpha or beta cells can be seen; however, most cells are organized as aggregates or more frequently as islets. The size of these islets is extremely variable; some of them are small (A) and others present different shapes (in panels B, C and D). Although glucagon cells are seen in the periphery of these islets, in some cases alpha cells are intermingled with beta cells. Importantly, the present results show that the size and cellular composition of canine islets varies according to their location in the pancreas. Moreover, islets are more numerous in the right lobe of the canine pancreas.

3—Discussion

In the mammalian pancreas, endocrine cells are grouped into islets of Langerhans, which are embedded in the exocrine tissue, and secrete insulin, glucagon and other polypeptide hormones into the bloodstream. This structure has been quite extensively studied in adult mammals and is conserved across species (Steiner et al., 2010; Kim A. et al., 2010). By contrast, although the development of the foetal and postnatal endocrine pancreas has been examined in depth in rodents (Pictet et al., 1972) and human (Hawkins et al., 1987; Justice et al., 1997), it is largely ignored in other mammals. The objective of this work was to describe the differentiation and growth of canine alpha and beta cells from early foetal to post-natal life.

Since the pioneer work of Pictet and Rutter (Pictet et al., 1972) the morphological development of the pancreas has been studied in great details mainly in the mouse and is known to pass through three development stages.

The first phase or first transition period is an early undifferentiated stage when morphogenesis occurs. The pre-patterned endodermal epithelium of the foregut develops into branching ducts and undifferentiated epithelium. In the mouse this occurs between e8.5 and e12.5. During the Second transition, the buds begin to differentiate into endocrine and exocrine cellular lineages by e14 and pancreatic epithelium proliferate and expand extensively. By e15, in the mouse, the dorsal and ventral pancreatic rotate and fuse, and a nearly fully developed pancreas is form just before birth by e19. At that stage, the pancreas contains endocrine cells organised into isolated clusters that condense into the islets of Langerhans (third developmental transition). Finally, the maturation of endocrine cells and their acquisition of full nutrient responsiveness continue for 2-3 weeks after birth.

The results presented here show that at mid gestation (foetal age 30 and 33) epithelium is dense and rare beta cells can be observed. From 36 to 45 days pc the pancreas increases in size the epithelium expand and branches, both trunk and tips areas can be observed. This ontogenic pattern of the dog pancreas development is different from the ontogenic pattern of the human pancreas development. In human, the beta cells only appear at the beginning of the second trimester of gestation.

Immuno-histological observations are very informative but cannot indicate whether the transcriptional regulatory mechanisms governing pancreas development in the dog is comparable to the transcriptional regulatory pathways described in rodents. Further studies should be perused to identify the regulatory mechanism governing the canine pancreas development in the dog.

Immuno-cytochemical studies of the distribution of Insulin and Glucagon cells in a normal adult canine pancreatic islet has been described before (Hawkins et al., 1987; Justice et al., 1997). The present results are in accordance with anatomical reports stating that, in addition to fully formed islets, aggregates of few beta cells can be seen and also some isolated alpha cells. Most reports indicate that alpha cells (glucagon) were often located at the periphery of these islets. In the present study, alpha cells are found intermingled with beta cells in fully formed islets and not systematically located in the periphery. This is at variance to what has been reported (Hawkins et al., 1987; Justice et al., 1997). Yet, it is known that there is heterogeneity between the right and left lobe of the pancreas. Moreover, the present study reveals that islets are more numerous in the right lobe of the canine pancreas. Importantly, the present results show that the size and cellular composition of canine islets varies according to their location in the pancreas.

Although an attempt was made to use the same strain of dogs for all development stages in the present study, this was not always possible for practical reasons. Therefore, the pancreas development was compared in several breeds. Beagle's pancreases at foetal age 45 days pc were compared to a Labrador at a same foetal age. A similar comparison was performed at post-natal day 1 in a beagle and chow-chow. At both ages, a similar distribution of endocrine clusters was observed. At 45 days pc, a predominance of glucagon cells was observed, as well as the presence of beta and alpha cells forming aggregates, but no real islet structure. At post-natal day one, alpha and beta cells are equally represented and organized in clusters. Both cells tend to aggregates and formed islets although the full typical architecture of a mature islet is rarely observed. These results show that there are no major differences between common strains of dogs regarding pancreas development.

In conclusion, this study demonstrates that beta cells in foetal dogs are visible at mid gestation and that islets are formed a few days before delivery.

C) Production of Functional Insulinoma

A pancreas obtained from a dog foetus of 42 days post conception was transplanted under the kidney capsule of scid mice. A tumour developed after 2 months (FIG. 4A). The immunohistochemistry analyses reveal the presence of large amounts of insulin-secreting and glucagon-secreting cells (FIG. 4B). The presence of PDX transcription factor, which is normally found in an adult beta cell, shows that the pancreatic cells have a normal development (FIG. 4C). These results show that the canine foetal pancreas normally grows and matures, and possesses beta cells which express both insulin and PDX, when transplanted into scid mice.

The cells extracted from a pancreas obtained from a dog foetus of 45 days pc were transduced with a lentiviral vector that expressed SV40LT under the control of a 405-nucleotide-long fragment of the rat insulin II promoter. The immunohistochemistry analyses before transplant show that very few insulin-secreting cells are present in the pancreas at this stage (FIG. 5A). Two months after transplant of the resulting transduced pancreas tissues under the kidney capsule of scid mice, a tumour has formed (FIG. 5B). The immuno-histochemical analyses show the presence of insulinomas (insulin-secreting cells, light grey) and the expression of insulin and LargeT by the beta cells (white, FIG. 5C). Dog-specific insulin is detected in the serum of normally fed mice two months after transplant, confirming that the insulinomas produce dog-specific insulin. In contrast and as expected, no dog-specific insulin is found in mice before transplantation, and insulin levels increase in adult dog plasmas after meals as expected, showing the specificity of the dog-specific insulin assay (FIG. 6A). Glycaemia remains high (mean 0.5 g/L) in mice two months after transplant.

In conclusion, the assay of dog-specific insulin in the scid mouse carrying the insulinoma allows to predict the presence of the tumour and the developmental stage of the tumour.

Mice transplanted with a transduced pancreas tissue (Ecd38 and Edc49) have undergone fasting for 19 hours twelve months after transplant. Dog-specific insulin levels were assayed in the serum of the fasting mice. FIG. 6B shows that the level of dog-specific insulin is very low in the serum of fasting mice (Fasting Ecd38 and Ecd49 mice). The same mice express high levels of dog-specific insulin when normally fed for one month after the 19-hour fasting period. Thus, the levels of dog-specific insulin in grafted mice highly decrease during fasting periods and increase greatly upon feeding (FIG. 6B; Fasting Ecd38 and Ecd49 mice). The level of dog-specific insulin is very low in the serum of a control mouse transplanted with a non-transduced pancreas tissue, which is either fasting or non-fasting (FIG. 6B; Ecd 28 mouse). These results show that dog-specific insulin secretion by the insulinoma is regulated by glycaemia levels in transplanted mice.

D) Production of Functional Canine Beta Cell Lines

Insulinoma-like structures were obtained after transplant of SV40LT-transduced dog foetal pancreas cells under the kidney capsule of scid mice, as described in Example C) above. The insulinoma-like structures were micro-dissected and the cells were dissociated. The dissociated cells were sub-transplanted into the kidney capsule of new scid mice and newly developed insulinoma-like structures were obtained. The mice were sacrificed and the insulinoma-like structures were micro-dissected. The cells of the insulinoma-like structures were dissociated and the pancreatic beta cells were collected to form homogenous cell populations. These homogenous cell populations were cultured in vitro, either on Matrigel or on fibronectin coated plates in a serum free medium containing 5.5 mM glucose, BSA, nicotinamide, 2-mercaptoethanol, human transferin and sodium selenium, to establish dog beta cell lines. The dog beta cell lines were maintained and grown in culture in a medium free of serum, either on Matrigel or on fibronectin coated wells.

The dog beta cell lines developed were studied by immunohistochemistry. Cells were stained with an anti-insulin antibody (light grey) and the nucleus were stained with DAPI (dark grey; FIG. 7). FIG. 7 shows that high levels of insulin are detected in all the cells of the dog beta cell lines. Insulin staining is restricted to the cytoplasmic compartment of all the cells. Insulin expression is detected after more than 20 passages. These results show that the dog beta cell lines are homogeneous and that these cells are stably producing insulin. These data confirm that the dog beta cell lines obtained by using the method described above are fully functional and stable.

REFERENCES

Ahlgren K M, Fall T, Landegren N, Grimelius L, von Euler H, Sundberg K, Lack of evidence for a role of islet autoimmunity in the aetiology of canine diabetes mellitus PLoS One. (2014); 9(8):e105473;

Barbas et al., 2001, Phage Display: A Laboratory Manual

Beta-cell development: the role of intercellular signals.Diabetes Obes Metab. 2008 November; 10 Suppl 4:195-200.

Bonnet B N. Et Egenvall A. "Age patterns of disease and death in insured Swedish dogs, cats and horses", Department of Population Medicine, University of Guelph, Ontario, Canada J Comp Pathol. 2010 January; 142 Suppl 1:S33-8.

Bricout-Neveu E, Pechberty S, Reynaud K, Maenhoudt C, Lecomte M J, Ravassard P, and Czernichow P—Development of the Endocrine Pancreas in the Beagle Dog: From Fetal to Adult Life Anat Rec 2017 Mar. 14. doi: 10.1002/ar.23595.

Castaing, M., Duvillie, B., Quemeneur, E., Basmaciogullari, A., and Scharfmann, R. (2005). Ex vivo analysis of acinar and endocrine cell development in the human embryonic pancreas. Dev Dyn 234, 339-345.

Catchpole B., Ristic J M., Fleeman L M. Et Davison L J. "Canine diabetes mellitus: can old dogs teach us new tricks?" in Diabetologia, 2005; 48:1948-56;

Davison L J, Weenink S M, Christie M R, Herrtage M E, Catchpole B. Autoantibodies to GAD65 and IA-2 in canine diabetes mellitus. Veterinary immunology and immunopathology. (2008); 126:83-90

Davison L J., Herrtage M E. Et Catchpole B. "Study of 253 dogs in the United Kingdom with diabetes mellitus" inVet Rec. 2005; 156(15):467-71.

F. M. Ausubel et ah, eds., 1987 Current Protocols in Molecular Biology

Gale E. A. M. Do dogs develop autoimmune diabetes? Diabetologia (2005) 48: 1945-1947

Hawkins, K. L., Summers, A., P. Kuhajda, P., Smith, C. A. Immunocytochemistry of Normal Pancreatic Islets and Spontaneous Islet Cell Tumors in Dogs Vet. Pathol. 2170-179 (1987)

Justice, D., Cruccioli, N., Roque, C., Galls, J, F., Remaudet, B., Cahard, D. Etude morphometrique des ilots de Langerhans du pancréas du chien Beagle Rev Fr Histotechnology 1997, 10:45-49

Kennedy L J, Davison L J, Barnes A, Short A D, Fretwell N, Jones C A, et al. Tissue Antigens. Identification of susceptibility and protective major histocompatibility complex haplotypes in canine diabetes mellitus. (2006); 68(6): 467-76.

Khalfallah, O., Ravassard, P., Serguera-Lagache C., Fligny, C., Serre, A., Bayard, E., Faucon-Biguet, N., Mallet, J., Meloni, R., and Nardelli, J. (2009). Zinc finger protein 191 (ZNF191/2fp191) is necessary to maintain neural cells as cycling progenitors. Stem Cells 27:1643-1653

Kim A, Miller K, Jo J, Kilimnik G, Wojcik P, and Hara M Islet architecture: A comparative study Islets. 2009; 1(2): 129-136.

Methods in Enzymology (Academic Press, Inc.

Mullis et al, ed., 1994 PCR: The Polymerase Chain Reaction

Nelson R W and Reusch C E, (2014), Animal models of disease: classification and etiology of diabetes in dogs and cats. J Endocrinol. September; 222(3):T1-9. doi: 10.1530/JOE-14-0202.

Niessen S J., Powney S. Guitian J., Niessen A P., Pion P D., Shaw J A. Et Church D B. "Evaluation of a quality-of-life tool for dogs with diabetes mellitus" in J Vet Med. 2012; 26(4):953-61.

Perbal Bernard V., 1988, A Practical Guide to Molecular Cloning

Pictet, R. L., Clark, W. R., Williams, R. H., and Rutter, W. J. An ultrastructural analysis of the developing embryonic pancreas. Dev. Biol. 1972, 29, 436-467.

R. I. Freshney, ed., 1987 Animal Cell Culture

Rand J S, Fleeman L M, Farrow H A, Appleton D J, Lederer R. (2004) Canine and feline diabetes mellitus: nature or nurture? J Nutr. 2004 August; 134(8 Suppl):2072S-2080S.

Ravassard P, Emilie Bricout-Neveu, Hazhouz Y, Pechberty S, Mallet J, Czernichow P, Scharfmann R. (2009) A new strategy to generate functional insulin-producing cell lines by somatic gene transfer into pancreatic progenitors. PLoS One.4(3): e4731

Ravassard P, Hazhouz Y, Pechberty S, Bricout-Neveu E, Armanet M, Czernichow P, Scharfmann R.; (2011) A genetically engineered human pancreatic B cell line exhibiting glucose-inducible insulin secretion.J Clin Invest. 2011 September; 121(9):3589-97.

Remington's Pharmaceutical Science, 17$^{th}$ ed., Mack Publishing Company, Easton, Pa. (1985)

Russ, H. A., Bar, Y., Ravassard, P., and Efrat, S. (2008). In vitro proliferation of cells derived from adult human beta-cells revealed by cell-lineage tracing. Diabetes 57:1575-1583.

Sambrook et al, 1989, Molecular Cloning: A Laboratory Manual, second edition; M. J. Gait, ed., 1984, Oligonucleotide Synthesis Scharfmann R, Duvillie B, Stetsyuk V, Attali M, Filhoulaud G, Guillemain G. (2008)

Shield E J et al, Extreme Beta-cell deficiency in Pancreata of Dogs with canine Diabetes, PloS one (2015); 10, 1719

Steiner D J, Kim A, Miller K, Hara M Pancreatic islet plasticity: interspecies comparison of islet architecture and composition. Islets. 2010; 2(3):135-45

Zufferey, R., Nagy, D., Mandel, R. J., Naldini, L., and Trono, D. (1997). Multiply attenuated lentiviral vector achieves efficient gene delivery in vivo. Nat Biotechnol 15, 871-875.

The invention claimed is:

1. A method of preparing canine pancreatic beta cells or canine beta cell tumours, comprising the steps of:
   a) transducing or co-transducing immature canine pancreas cells with i) a lentiviral vector encoding SV40 LargeT antigen under the control of the insulin promoter, or ii) with a lentiviral vector encoding SV40 LargeT antigen under the control of the insulin promoter and a lentiviral vector encoding hTert under the control of the insulin promoter, or iii) a lentiviral vector encoding both SV40 LargeT antigen and hTert under the control of the insulin promoter wherein the immature canine pancreas cells are obtained from a foetal canine pancreas at days 40 to 60 post conception;
   b) introducing the transduced immature pancreas cells obtained in a) into the kidney capsule of a first severe combined immunodeficiency (scid) mouse;
   c) allowing the transduced immature pancreas cells to develop insulinoma-like structures, wherein the canine pancreas cells in insulinoma-like structures have differentiated to insulin-producing pancreatic beta cells;
   d) micro-dissecting the insulinoma-like structures obtained in step c), and dissociating the cells thereof;
   e) sub-transplanting the cells obtained in step d) into the kidney capsule of a second scid mouse;
   f) allowing the sub-transplanted cells in step e) to develop and regenerate newly developed insulinoma-like structures, wherein said newly developed insulinoma-like structures are enriched in insulin-producing pancreatic beta cells;
   g) micro-dissecting the insulinoma-like structures obtained in step f), and dissociating and collecting the cells thereof.

2. The method according to claim 1 wherein the immature canine pancreas cells are immature dog pancreas cells.

3. The method according to claim 1 wherein the immature canine pancreas cells are obtained from a portion of the right lobe (or head) of the pancreas or the entire right lobe (or head) of the pancreas.

4. The method according to claim 1, wherein the immature canine pancreas cells are obtained from a foetal canine pancreas at days 40 to 55 post conception.

5. The method according to claim 1, wherein the construction of the lentiviral vectors allows reversible or conditional immortalization.

6. The method according to claim 1, wherein the lentiviral vectors comprise at least one Lox P site and the SV40 LargeT and/or hTERT genes are removed by the action of the Cre recombinase.

7. The method according to claim 1, wherein the lentiviral vectors comprise at least one FRT site and the SV40 LargeT and/or hTERT genes are removed by the action of the FLP recombinase.

8. The method according to claim 1, wherein the lentiviral vector encoding SV40 LargeT and the lentiviral vector encoding hTERT further comprise a LoxP or a FLP site, provided that the site-specific recombination sites are different in said vectors.

9. The method according to claim 6, wherein a negative selection step is performed after the action of the Cre or FLP recombinase to select only the cells in which the immortalization genes SV40 LargeT and/or hTERT have been removed.

10. The method according to claim 6, wherein said lentiviral vectors include at least one negative selection marker gene.

11. The method according to claim 10, wherein said negative marker gene is selected from the group constituted by the HSV-TK gene, the hypoxanthine phosphoribosyl transferase (HPRT) gene, the guanine-phosphoribosyl-transferase (Gpt) gene, and the cytosine deaminase gene.

12. The method of claim 1, further comprising the step of:
  h) repeating step e), f) and g) until the appropriate amount of insulin-producing pancreatic beta cells is obtained.

* * * * *